United States Patent [19]

Sweet et al.

[11] Patent Number: 4,882,377
[45] Date of Patent: Nov. 21, 1989

[54] LOW-VISCOSITY PRESSURE-ADHERENT SILICONE ELASTOMER COMPOSITIONS

[75] Inventors: Randall P. Sweet; Patrick J. Miller, both of Midland, Mich.; Virgil L. Metevia, Chino, Calif.

[73] Assignee: Dow Corning Corporation, Midland, Mich.

[21] Appl. No.: 247,184

[22] Filed: Sep. 21, 1988

[51] Int. Cl.$^4$ ............................................. C08K 5/54
[52] U.S. Cl. ................................. 524/267; 524/268; 524/290; 524/315; 524/356; 524/362; 524/366; 524/376; 524/377; 524/379; 525/477; 525/478
[58] Field of Search .............. 525/477, 478; 524/267, 524/268, 379, 366, 356, 315, 376, 377, 362, 290

[56] References Cited

U.S. PATENT DOCUMENTS

| | | | |
|---|---|---|---|
| 3,527,659 | 9/1970 | Keil | 117/145 |
| 4,331,651 | 5/1982 | Reul et al. | 424/19 |
| 4,418,157 | 11/1983 | Modic | 521/82 |
| 4,584,355 | 4/1986 | Blizzard et al. | 525/477 |
| 4,585,836 | 4/1986 | Homan et al. | 525/477 |
| 4,591,622 | 5/1986 | Blizzard et al. | 525/477 |
| 4,593,049 | 6/1986 | Bauman et al. | 521/99 |
| 4,608,396 | 8/1986 | Bauman et al. | 521/99 |
| 4,655,767 | 4/1987 | Woodard et al. | 604/896 |

FOREIGN PATENT DOCUMENTS

| | | | |
|---|---|---|---|
| 711756 | 6/1965 | Canada | 400/69 |
| 03477 | 6/1987 | PCT Int'l Appl. | |

OTHER PUBLICATIONS

"New Pressure-Sensitive Silicone Adhesive", Langley Research Center, Hampton, Va.; NASA Tech Briefs Winter, 1980, pp. 452-453.
"Information About Fluorosilicone Elastomers", Product Bulletin Form No. 17-325-81, (1981), Dow Corning Corp., Midland, Mich., 4 pages.
"Information About High Technology Silicone Materials", Product Bulletin Form No. 10-052B-85, (1985), Dow Corning Corp., Midland, Mich., 6 pages.

*Primary Examiner*—Melvyn I. Marquis
*Attorney, Agent, or Firm*—Susan M. Cornwall

[57] ABSTRACT

A pressure-adherent silicone elastomer composition comprising a homogeneous mixture of a silicone pressure sensitive adhesive composition, a crosslinkable silicone elastomer composition, and, optionally, a viscosity reducing agent. Specifically, the silicone pressure sensitive adhesive composition is a condensation product, having a plasticity of less than 200 mils, of a benzene-soluble resinous copolymer containing silicon-bonded hydroxyl radicals and consisting essentially of triorganosiloxy units of the formula $R_3SiO_{\frac{1}{2}}$ and tetrafunctionalsiloxy units of the formula $SiO_{4/2}$ in a ratio of about 0.6 to 0.9 triorganosiloxy units for each tetrafunctionalsiloxy unit present in the copolymer and a polydiorganosiloxane having a viscosity from 100 centipoise to 50,000 centipoise at 25° C.

18 Claims, No Drawings

LOW-VISCOSITY PRESSURE-ADHERENT SILICONE ELASTOMER COMPOSITIONS

BACKGROUND OF THE INVENTION

The present invention relates to silicone compositions which, when cured, exhibit pressure sensitive adhesive properties and are of an elastomeric nature.

Silicone pressure sensitive adhesives have found use in medical devices which adhere to a patient's skin, such as transdermal drug delivery patches. Transdermal drug delivery patches are typically composed of a non-permeable cover which covers a reservoir of drug. The cover typically has a rim extending beyond the reservoir which has a silicone pressure sensitive adhesive (SPSA) on the surface which is to be applied to the patient's skin. The device also has, attached to the SPSA, an impermeable backing layer having a release coating thereon, the backing layer being removed prior to adhering the device to the skin. The reservoir may be a material (e.g. elastomeric) impregnated with the drug, ofter referred to as a "matrix", or it may be a solution of the drug. Between the reservoir and the patient's skin, there is ofter a membrane through which the drug travels from the reservoir to the patient. This membrane may be formed of a silicone pressure sensitive adhesive.

To reduce the number of component parts and make assembly easier, it is desirable to have a material that would provide both pressure sensitive adhesive and elastomeric properties which could be used to form either a membrane or a matrix for transdermal drug delivery devices. Current volatile solvent-containing SPSA's often exhibit formation of bubbling when cured into thick sections as would be needed for the matrix of a matrix type transdermal drug delivery device, resulting in a non-uniform product. Some current SPSA's have also been found to lose cohesiveness and, ofter, detackify with the addition of many drugs and/or excipients used in the pharmaceutical industry, such as non-ionic surfactants, e.g. isopropylpalmitate. The inclusion of drugs or excipients ofter results in dissolving the SPSA's, causing them to flow and lose their original shape even at room temperature.

Some prior art SPSA's have also been known to aggressively adhere to substrates, especially with age, which is usually undesirable, resulting in increased difficulty in removal from the substrate, whether it be, e.g., a patient's skin or paper. Therefore, there is need for SPSA's having controllable aggressiveness.

In the past, activity at the National Aeronautics and Space Administration (NASA) Langley Research Center has focused on forming PSA's having some elastomeric quality. Such activity is disclosed in U.S. patent application Ser. No. 569,536, entitled "Structural Pressure Sensitive Adhesives" filed Jan. 12, 1984, now abandoned, as NASA Case LAR-13,270-1. The specification and abstract of this application was made public when its public availability was announced in 1984 in NASA Patent Abstracts Bibliography, NASA Publication No. SP-7039(31), as Accession No. N84-32532. The application discloses the blending of an intermediate molecular weight pressure sensitive silicone adhesive with a silicone system which generally cures with a catalyst to a rubber tack-free state, to form a pressure sensitive silicone adhesive. The application discloses as a specific example, the blend of SR6574 (described in the application as a liquid, tacky silicone gum or uncrosslinked resin system which contains 44–46% volatiles and is available from General Electric under the tradename Silgrip), RTV 560, (described as a liquid silicone rubber also available from General Electric), and a catalyst employed to cure the RTV 560 portion but not cure the SR6574 component.

The application also discloses that Dow Corning RTV 3120 (with catalyst) and "Silastic LS420 Gum (a Dow Corning tradename fluorosilicone rubber)" may be substituted, respectively, for the RTV 560 and SR6574, and that General Electric's SR595, described as another pressure sensitive adhesive, may be employed in lieu of the SR6574. Additionally, the application discloses that silicone resins which cure with platinum compounds via ≡SiH to ≡SiVi or acetoxy- or alkoxy-containing silicones which cure with moisture may be employed as the curing resin.

As disclosed in Dow Corning Corporation's Product Brochure Form No. 10-052B-85 (1985), DOW CORNING ® 3120 is a two-part room temperature vulcanizing (RTV) silicone rubber which can be catalyzed by stannous octoate or dibutyl tin dilaurate. As disclosed in Dow Corning Corporation's Product Brochure Form No. 17-325-81 (1981), SILASTIC ® LS-420 Fluorosilicone Gum is a silicone polymer with methyl, trifluoropropyl, and vinyl substituents.

The PSA compositions taught in the NASA application contain volatile solvents. The presence of the volatile solvent can result in bubbling in thick sections prepared from the PSA.

SUMMARY OF THE INVENTION

In view of prior PSA's and the continuing needs of the pharmaceutical industry, there remains a need for a silicone pressure sensitive adhesive composition which is free of volatile components, can be formulated to maintain tack and cohesiveness with the addition of many types of drugs or excipients, has a means for controlling the aggressiveness of the adhesive, and has a low viscosity to facilitate processing. A low viscosity composition would allow for easier mixing with active ingredients or excipients and generally not require high shear mixing, would be easily molded or casted onto a substrate (e.g. coated onto paper backing) without heating the composition.

It is also highly desirable to have available a silicone PSA composition that, for general purposes, is free of flammable components, can be formulated to consist primarily of silicone components, and can be formulated so that the cured composition will maintain its shape, tack, and adhesion even through moist or wet conditions.

It is also highly desirable to have available a silicone PSA composition that, for the purpose of forming a matrix material for controlling the delivery of a bioactive agent to a substrate, can be cured at relatively low temperatures so as not to destroy the bioactive agent incorporated into the PSA composition.

It is further highly desirable to have available a silicone PSA composition that, for the purpose of forming the adhesive, membrane, and/or matrix for transdermal drug delivery systems, can be formulated to hove a degree of adhesion and tack which is suitable for adhering to and removing from a patient's skin and which does not increase undesirably in adhesion with time, causes little or no skin irritation, swelling, or redness, and leaves little or no adhesive residue on the skin after removal.

These and other objects are provided by the invention which is a pressure-adherent silicone elastomer composition comprising a homogeneous mixture of a silicone pressure sensitive adhesive composition, a crosslinkable silicone elastomer composition, and, optionally, a viscosity reducing agent. Specifically, the silicone pressure sensitive adhesive composition is a condensation product, having a plasticity of less than 200 mils, of a benzene-soluble resinous copolymer containing silicon-bonded hydroxyl radicals and consisting essentially of triorganosiloxy units of the formula $R_3SiO_{\frac{1}{2}}$ and tetrafunctionalsiloxy units of the formula $SiO_{4/2}$ in a ratio of about 0.6 to 0.9 triorganosiloxy units for each tetrafunctionalsiloxy unit present in the copolymer and a polydiorganosiloxane having a viscosity from 100 centipoise to 50,000 centipoise at 25° C.

The invention disclosed herein also provides for a method of making the pressure-adherent silicone elastomer compositions, for the pressure-adherent silicone elastomer composition further containing a bioactive agent, for the method of controlling the delivery of bioactive agents using the pressure-adherent silicone elastomer composition, and for a transdermal drug delivery device using the pressure-adherent silicone elastomer composition.

DETAILED DESCRIPTION OF PREFERRED EMBODIMENTS OF THE INVENTION

More specifically, the invention provides a pressure-adherent silicone elastomer composition comprising a homogeneous mixture of (I) a silcone pressure sensitive adhesive composition employed in an amount from about 15 to about 90 parts by weight, the silicone pressure sensitive adhesive composition comprising a homogeneous mixture of (A) from about 35 to about 70 parts by weight of at least one benzene-soluble resinous copolymer containing silicon-bonded hydroxyl radicals and consisting essentially of triorganosiloxy units of the formula $R_3SiO_{\frac{1}{2}}$ and tetrafunctionalsiloxy units of the formula $SiO_{4/2}$ in a ratio of about 0.6 to 0.9 triorganosiloxy units for each tetrafunctionalsiloxy unit present in the copolymer and (B) from about 30 to about 65 parts by weight of at least one polydiorganosiloxane consisting essentially of ARSiO units terminated with endblocking $TRASiO_{\frac{1}{2}}$ units, each said polydiorganosiloxane having a viscosity of from about 100 centipoise to about 50,000 centipoise at 25° C. where each T is —OH or —OR', where each R is a monovalent organic radical selected from the group consisting of hydrocarbon radicals of from 1 to 6 inclusive carbon atoms, each R' is an alkyl radical of from 1 to 4 inclusive carbon atoms, and each A radical is selected from the group consisting of R- and halohydrocarbon radicals of from 1 to 6 inclusive carbon atoms, the silicone pressure sensitive adhesive composition having been reaction-condensed to a plasticity of not more than about 200 mils at 23° C. as measured after force is applied on a specimen weighting twice the specific gravity of the silicone pressure sensitive adhesive composition for 3 minutes ±5 seconds, (II) a crosslinkable silicone elastomer composition employed in an amount from about 10 to about 85 parts be weight, the total of silicone pressure sensitive adhesive composition (I) and crosslinkable silicone elastomer composition (II) being 100 parts by weight, and (III) a non-volatile, nonflammable, compatible viscosity reducing agent for reducing the viscosity of said pressure-adherent silicone elastomer composition employed in an amount from 0 to about 40 weight percent based on the total weight of the silicone pressure sensitive adhesive composition (I) and the crosslinkable silicone elastomer composition (II), said viscosity reducing agent being generally non-reactive with said silicone pressure sensitive adhesive composition (I) and said crosslinkable silicone elastomer composition (II).

More preferred compositions employ from 40 to 80 parts be weight of the silicone pressure sensitive adhesive composition (I) and from 20 to 60 parts by weight of the crosslinkable silicone elastomer composition (II).

The silicone pressure sensitive adhesive composition (I) used in the invention comprises a reaction-condensed mixture of a benzene-soluble resinous copolymer and a polydiorganosiloxane. The reaction condensation may be carried out as described in Canadian Pat. No. 711,756 to Pail which is hereby incorporated be reference.

To carry out the condensation reaction, preferably, the benzene-soluble resinous copolymer and the polydiorganosiloxane are mixed with a silanol condensation catalyst such as an acid or base and, while continuing to be mixed, heated above 100° C. and maintained at 100° C. from one to several hours until the desired adhesive is formed. The desired adhesive is easily recognized by one skilled in the field of pressure-sensitive adhesives. Suitable silicone pressure sensitive adhesive compositions (I) are prepared by condensing the mixture until the mixture reaches a plasticity of at least about 50 mils at 23° C. as measured after force is applied on a specimen weighing twice the specific gravity of the pressure sensitive adhesive composition for 3 minutes ±5 seconds using ASTM D926). Silicone pressure sensitive adhesive compositions (I) having lower plasticities may work as well.

ASTM D926 is a test which measures the plasticity of materials by means of a parallel plate plastometer. In ASTM D926, the material is allowed to rest for a specified time and then is subjected to a compressive force of 49 N for a specified time. At the end of this time, the thickness of the specimen is taken as a measure of the plasticity. For measuring the plasticity for this invention, a parallel plate plastometer from Scott Tester, Inc., Providence, R.I., Catalog No. C 544445 was used, and the material was allowed to rest for 1 hour at 23° C. before measuring.

Preferably, the condensation takes place under reflux conditions, so that condensation by-products are removed from the mixture. Preferred duration for the condensation process is between 1 and 10 hours. The condensation reaction is terminated before or at the point when the silicone pressure sensitive adhesive composition (I) achieves a plasticity of 200 mils. Preferably the silicone pressure sensitive adhesive composition (I) has a plasticity of less than 180 mils, and more preferably less than 150 mils at 23° C.

Examples of suitable silanol condensation catalysts for the condensation reaction are hydrogen chloride, ammonia, ammonium carbonate, or amines, such as aliphatic organic amino compounds, including secondary amines, tertiary amines, carboxylic acid salts of these amines and quaternary ammonium salts. The silanol condensation catalyst is typically added from 0.001 to 5 weight percent based on the weight of the resin copolymer and the polydiorganosiloxane.

As previously mentioned, the viscosity of the polydiorganosiloxane is from 100 to 50,000 cp at 25° C. More preferably, the viscosity of the polydiorganosiloxane is from 100 centipoise to 20,000 centipoise at 25° C., and most preferably the viscosity of the polydiorganosiloxane is from 100 centipoise to 15,000 centipoise at 25° C.

Crosslinkable silicone elastomer composition (II) may be selected from various silicone elastomer compositions, which generally comprise a reactive polydiorganosiloxane (PDOS), a crosslinking agent, and, if necessary, a catalyst wherein the reactive polydiorganosiloxane reacts with the crosslinking agent to form a crosslinked silicone elastomer. It is necessary that the crosslinkable silicone elastomer composition (II) be curable by a chemistry which will not cure the silicone pressure sensitive adhesive composition (I) to the point of eliminating tack or adhesive properties.

By varying the level of crosslinking agent, various degrees of curing, and ofter, various degrees of tack can be achieved with the pressure-adherent silicone elastomer composition. Generally, once one reaches the point of adding less than the stoichiometric amount of crosslinking agent needed for cure, a decrease in the crosslinking agent level, will result in an increase in tack of the final product.

A preferred crosslinkable silicone elastomer composition (II) is based on silicon-bonded alkenyl to ≡SiH cure chemistry and comprises (a) an alkenyl-containing polydiorganosiloxane containing at least two alkenyl radicals per molecule, (b) an organohydrogensiloxane in an amount sufficient to cure the crosslinkable silicone elastomer composition (II) in the presence of a hydrosilation catalyst, and (c) a catalytically effective amount of a hydrosilation catalyst. Such compositions are well known in the art.

The organo radical of the alkenyl-containing polydiorganosiloxane is a radical of from 1 to 6 inclusive carbon atoms. For example, the organo radical may be methyl, ethyl, propyl, 3,3,3-trifluoropropyl, or phenyl. Preferably, the alkenyl radical is vinyl ("Vi") and the organo radical is methyl ("Me"). More preferably, the vinyl radicals are located at the terminal positions on the polydiorganosiloxane. In addition to having diorganosiloxane units, the polymer can include small amounts of triorganosiloxy, monomethylsiloxy, and $SiO_{4/2}$ units.

The organohydrogensiloxane contains an average of more than two silicon-bonded hydrogen atoms per molecule. Preferably, the organohydrogensiloxane has at least three silicon-bonded hydrogen atoms per molecule and the organo group is methyl. The organohydrogensiloxane includes homopolymers, copolymers, and mixtures thereof. Preferred organohydrogensiloxanes are trimethylsiloxy-endblocked copolymers containing dimethylsiloxane and methylhydrogensiloxane units.

The hydrosilation catalyst is a platinum- or rhodium-containing material. Any of the known platinum-containing catalysts will promote the curing. One of the preferred catalysts are complexes formed by reacting chloroplatinic acid with a vinyl-terminated polydiorganosiloxane. Catalysts of this type are described in U.S. Pat. No. 3,419,593 to Willing. Typically, the catalyst concentration is equivalent to more than about 0.1 parts by weight of platinum per million parts by weight of the crosslinkable silicone elastomer composition (II).

Rhodium-containing catalysts suitable for use in the crosslinkable silicone elastomer composition (II) include those disclosed in U.S. Pat. No. 4,026,835, to Lee, et al.

The crosslinkable silicone elastomer composition (II) based on alkenyl to ≡SiH cure chemistry may optionally include finely divided fillers, such as silica. Fumed silica, especially trimethylsiloxy-treated fumed silica is preferred. Other suitable fillers include glass fibers and carbon black.

Although some alkenyl (e.g. vinyl) groups on the silicone pressure sensitive adhesive composition (I) may be tolerated when employing crosslinkable silicone elastomer compositions based on alkenyl to ≡SiH cure chemistry in the invention, care should be taken that the amount of alkenyl groups on the silicone pressure sensitive adhesive composition (I) is not so great that the entire pressure-adherent silicone elastomer composition cures to the extent that the cured product exhibits no tack or pressure-sensitive adhesion.

The crosslinkable silicone elastomer composition (II) may also be a composition which cures via the Michael addition reaction, e.g. as that described in U.S. Pat. No. 4,698,406 to Lo, et al. which is hereby incorporated by reference. The curable silicone compositions disclosed in this patent comprise an amine-functional organopolysiloxane and an acryl-functional organopolysiloxane.

Another suitable crosslinkable silicone elastomer composition (II) is based on tin-catalyzed, silicone compositions which cure via acetoxy-moisture cure chemistry which are well-known in the art. Examples of such elastomer compositions are taught in U.S. Pat. No. 3,035,016 to Bruner, U.S. Pat. No. 3,636,134 to Antonen, U.S. Pat. No. 3,133,891 to Ceyzeriat, and U.S. Pat. No. 3,274,145 to Dupree which are hereby incorporated by reference. The elastomer compositions comprise a siloxane polymer having endblocking acetoxysiloxane units of the formula

where y has an average value from 1.8 to 2 inclusive and R''' is an organic radical selected from the group consisting of alkyl radicals having from 1 to 5 inclusive carbon atoms, phenyl radicals and vinyl radicals.

Such elastomer compositions may be prepared by reacting siloxane polymers terminated with hydrolyzable groups with monoorganotriacetoxysilanes. Optionally, the elastomer composition may contain, e.g., a filler, a silicone resin, or a catalyst.

Another well-known crosslinkable silicone elastomer composition which may also be used in the invention is a one-part system which cures via the titanate to alkoxy cure chemistry. For example, room-temperature curing compositions comprising hydroxyl-endblocked polydiorganosiloxane, a silane or silane mixture having greater than 2 alkoxy radicals per molecule, and a titanate compound which are cured upon exposure to moisture can be used in this invention. Such compositions are taught in U.S. Pat. No. 4,391,937 to Falender, et al. and U.S. Pat. No. 3,334,067 to Weyenberg, which are hereby incorporated by reference to teach of suitable crosslinkable silicone elastomer compositions for this invention.

Another crosslinkable silicone elastomer composition suitable for this invention and using a titanate, comprises an alkoxy-containing polydiorganosiloxane having at least 2 alkoxy units per molecule, and a titanate, such as tetraisopropyltitanate or tetrabutyltitanate. The alkoxy-containing polydiorganosiloxane may have the alkoxy groups as endgroups or pendent along the chain.

Crosslinkable silicone elastomer composition (II) may also be a two-part system based on ≡SiOH to alkoxy cure chemistry, which compositions typically comprise a hydroxy-containing PDOS fluid (preferably, endcapped with silicon-bonded hydroxyl groups), an alkoxy-containing organosilicon compound crosslinking agent having an average of more than two silicon-bonded alkoxy units per molecule, and a condensation catalyst. These crosslinkable silicone elastomer compositions are also well-known in the art.

Suitable alkoxy-containing organosilicon compounds are silanes of the formula $(R^5O)_3SiR^6$, orthosilicates of the formula $(R^5O)_4Si$, or polymers or mixtures thereof where $R^5$ is selected from monovalent hydrocarbon and halogenated hydrocarbon radicals having 6 carbons or less and radicals of the formula $-CH_2CH_2OR$ where R is a monovalent organic radical selected from the group consisting of hydrocarbon radicals of from 1-6 inclusive carbon atoms, as defined before, and where $R^6$ is hydrogen or any monovalent hydrocarbon or halogenated hydrocarbon radical having 6 carbons or less. Each of the $R^5$, $R^6$, and R radicals may be the same or different. It is preferred that both $R^5$ and $R^6$ are hydrocarbon radicals of less than 6 carbon atoms. It is most preferred that $R^5$ is a hydrocarbon of 3 or less carbon atoms. Examples of suitable organosilicon compounds are methyltrimethoxysiloxane, tetramethoxysilane, N-propylorthosilicate, ethylorthosilicate, methylpolysilicates, ethylpolysilicates, propylpolysilicates, and butylpolysilicates.

The alkoxy-containing organosilicon crosslinking agent must be employed in an amount sufficient to cure the crosslinkable silicone elastomer composition (II) in the presence of the condensation catalyst.

The condensation catalyst may be selected from the group consisting of organic acids, bases, and metal salts of carboxylic acid, such as zinc octoate, lead-2-ethyl hexoate, lead naphthenates, dibutylditindiacetate, dibutyltindilactate, stannous octoate, zinc napthanate, and ferrous octoate. For most applications, the catalyst is employed in amounts from 0.1 to 2 percent by weight based on the weight of the hydroxyl-containing polydiorganosiloxane.

Optionally, these types of crosslinkable silicone elastomer compositions include a filler, such as silica or alumina.

Consideration must be made when selecting the type of crosslinkable silicone elastomer composition (II) employed to ensure that there is not undesirable reaction between the crosslinkable silicone elastomer composition (II) and the silicone pressure sensitive adhesive composition (I) used resulting in premature gelation during processing or loss of physical properties after curing.

As discussed with some of the types of crosslinkable silicone elastomer compositions (II) above, the compositions may contain a filler or fillers, such as treated or untreated silica, glass fibers, carbon black, or alumina. If a silica filler is to be treated, the treating may be done in situ or the filler may be pre-treated, both techniques being known in the art. It is preferred in many cases to use a treated silica filler to prevent crepe hardening.

Although not meant to be limiting, prefereably, the pressure-adherent silicone elastomer composition, prior to initiating cure has a viscosity of less than 20,000 poise at 25° C. which is the maximum viscosity desired for room temperature processing and molding. More preferably, the composition has a viscosity of less than 10,000 poise at 25° C., and most preferably, the the composition has a viscosity of less than 3,000 poise at 25° C. 3,000 poise is a viscosity suitable for room temperature casting, i.e. applying the composition to a substrate and leveling off with an edge (such as a knife edge) to a layer of a thickness of about 0.005" or less, as is done in the tape industry. Generally, the viscosities discussed here are as measured using a BROOKFIELD Synchro-lectric Viscometer, Model HAF (available from Brookfield Engineering Inc., Stoughton, Massachusetts).

The compositions of the invention do not require the presence of volatile solvents (solvents which are removed prior to forming the final product). Generally, by "volatile" the applicants means those materials which vaporize readily at the temperatures of curing the pressure-adherent silicone elastomer composition. Preferred in most cases are those materials which have boiling points greater than about 100° C. at 760 mm Hg pressure.

The optional viscosity reducing agents for reducing the viscosity of the pressure-adherent silicone elastomer composition are materials or mixtures of two or more materials which are not volatile at the temperature of curing, are nonflammable, are compatible in the pressure-adherent silicone elastomer composition, and are generally nonreactive toward the other components of the composition. Flammable materials are those materials which are flammable according to the definition provided in United States Code of Federal Regulations, Title 49, Part 173, Section 115 (49 CFR 173.115). Briefly restated, a flammable liquid means any liquid having a flash point below 100° F., where flash point means the minimum temperature at which a liquid gives off vapor within a test vessel in sufficient concentration to form an ignitable mixture with air near the surface of the liquid. The CFR provides proper testing conditions for measuring flash point.

Suitable viscosity reducing agents (III) include liposoluble, scarcely hydrosoluble alcohols, esters, ethers, and ketones, e.g. as taught in U.S. Pat. No. 4,331,651 to Reul, et al. which is hereby incorporated by reference. Specifically, Reul, et al. teaches that examples of liposoluble, scarcely hydrosoluble alcohols, esters, ethers, and ketones include alcohols selected from the group consisting of 2-octyldodecanol, oleyl alcohol and phenylethanol, and esters selected from the group consisting of myristic acid isopropyl ester, caprylic/capric acid laurylstearyl ester, lauric acid hexyl ester, propionic acid myristyl ester, isostearic acid ethyl-lauryl ester, oleic acid ethyl ester, acetic acid phenyl ester, benzoic acid benzyl ester, salicylic acid methyl ester, lauric acid mono-1,1-propanediol ester, fatty acid polyethyleneglycol ester, caprylic/capric acid-1,2-propanediol diester, caprylic/capric acid glycerol monoester, lauric acid glycerol diester, butyric acid glycerol triester, caprylic/capric/lauric acid glycerol triester, acetic/stearic/oleic acid glycerol triester, adipic acid dibutyl ester, sebacic acid dibutyl ester, phthalic acid ester, citric acid triethyl ester, and ethers selected from the group consisting of didecyl ether, fatty alcohol polyethyleneglycol ether, alkyl-aryl polyethyleneglycol ether and anisol and ketones such as methylnonylketone.

Other suitable viscosity reducing agents (III) include polydiorganosiloxanes and polysilicates. An example of a suitable polydiorganosiloxane is polydimethylsiloxane. Polydimethylsiloxanes having a viscosity as low as about 5 cSt. have been found suitable for this invention. Especially suitable polydiorganosiloxanes are polydimethylsiloxane fluids having viscosities between about 5 cSt. and about 400 cSt.

Polysilicates are any alkyl polysilicates in which the alkyl radicals each contain less than 6 carbon atoms. Polysilicates are polymeric materials in which the silicon atoms are linked through Si—O—Si linkages, the remaining valences of the silicon being satisfied primarily by alkoxy radicals. Examples of polysilicates which would be suitable as the viscosity reducing agent (III) are diethoxydimethylsilicate, ethylorthosilicate, and N-propylorthosilicate.

The preferred class of viscosity reducing agents for medical applications and for efficiency in reduction of viscosity (III) are those esters which are fluid at 25° C. and have the formula:

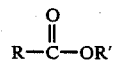

wherein R is a monovalent hydrocarbon radical having from 2 to 32 carbon atoms, and R' is a monovalent hydrocarbon radical having from 1 to 14 carbon atoms. More preferably, R has from 10 to 19 carbon atoms and R' has from 1 to 3 carbon atoms.

Levels of the viscosity reducing agent (III) will depend on the type of viscosity reducing agent used, the type of elastomer used, the properties of the silicone pressure sensitive adhesive composition (I), the relative amounts of the components in the composition of the invention, and the nature of any other component added to the composition of the invention.

Since the addition of a viscosity reducing agent tends to effect the tack and adhesion of the pressure-adherent silicone elastomer composition, adding a viscosity reducing agent (III) provides another advantage to the compositions of this invention, and that is, by selecting the type and amount of viscosity reducing agent (III), one has further control of the resulting adhesion of the cured material and the delivery rate of a bioactive agent through the cured material. To maintain adhesion, tack, and cohesive nature, it has been found that the viscosity reducing agent (III) should generally be at most about 40 weight % based on the total weight of the silicone pressure sensitive adhesive composition (I) and the crosslinkable silicone elastomer composition (II), and more preferably, between 3 and 10 weight percent. As higher amounts of the viscosity reducing agent (III) are used, relatively more of the crosslinkable silicone elastomer composition (II) and, correspondingly, less of the silicone pressure sensitive adhesive composition (I) may be required in order to maintain the cohesive strength of the pressure-adherent silicone elastomer composition.

In compositions of this invention, the tack and adhesion properties can be enhanced by techniques which are known in PSA art. One way of increasing tack and adhesion would be to add tackifiers other than the silicone pressure sensitive adhesive composition (I). Another method would be to undercrosslink the elastomer (i.e. adding less than the stoichiometric or usual amount of crosslinking agent to the reactive PDOS). A third approach may be the addition of the viscosity-reducing agent.

Other well-known ingredients such as pigments, inhibitors, adhesion promoters, water-soluble hydrocolloid gums, and other supplementary pressure sensitive adhesives, either organic or silicone-based, may be added to the pressure-adherent silicone elastomer composition of the present invention provided that such materials do not undesirably affect the adhesive and cohesive properties of the composition. Pressure sensitive adhesives are those materials which exhibit tack, adhesion with applied pressure, and will release subsequent to adhesion. Examples of organic materials used to form pressure sensitive adhesives include natural rubber, styrene-butadiene rubber, acrylonitrile rubber, polyurethane rubber, and polyisobutylene which either possess dry tack by themselves or develop such tack upon the addition of a plasticizer. The optimum level of addition of the supplementary pressure sensitive adhesive materials will depend on the type used. In many instances, there is a level of addition above which the cure of the composition will be inhibited or the organic and silicone materials will phase separate.

The pressure-adherent silicone elastomers may be made by mixing the ingredients in any order. The crosslinkable silicone elastomer composition (II) does not have to be pre-mixed before mixing with the other ingredients; instead the ingredients which make up the crosslinkable silicone elastomer composition (II) may be added to the composition in any order. Preferably, in the mixing step (1), a particular ingredient is added last, e.g. the crosslinking agent or the catalyst, because once it is mixed with the other ingredients, curing may start. The particular ingredient, although added last, can be mixed with other components before it is added.

Specifically, the pressure-adherent silicone elastomers of the invention may be prepared by: (1) homogeneously mixing the silicone pressure sensitive adhesive composition (I) with the ingredients which comprise the crosslinkable silicone elastomer composition (II), the viscosity reducing agent (III), and any other optional ingredients, such as a bioactive agent, (2) shaping the pressure-adherent silicone elastomer composition in the desired form for curing, and (3) curing the composition for a sufficient time to form the pressure-adherent silicone elastomer.

Shaping the composition in the desired form for curing (step 2) may be done in any manner desired and may utilize any of many types of molding techniques known, e.g., transfer, compression, extrusion, or injection molding or may be done manually.

The curing conditions will vary depending on the type of crosslinkable silicone elastomer composition (II) employed. For crosslinkable silicone elastomer compositions (II) which cure via ≡SiH to ≡SiVi, temperatures of 100° C. or less are suitable. Some of the types of crosslinkable silicone elastomer compositions cure at room temperature. The low-temperature curing characteristic of many of the compositions of this invention provides the advantage of being suitable for the incorporation of many bioactive agents or drugs which are sensitive to higher temperatures.

In one method of making the pressure-adherent silicone elastomers, (1a) the silicone pressure sensitive adhesive composition (I), a mixture of the reactive PDOS, the catalyst, and a filler, and a viscosity reducing agent (III), are homogeneously mixed together; (1b) the homogeneous mixture is devolatilized, if necessary;

(1c) a mixture of the reactive PDOS, a crosslinking agent, and an inhibitor is homogeneously mixed with the devolatilized mixture; (2) the composition is shaped as desired; and (3) the composition is cured.

In another method, (1a) the silicone pressure sensitive adhesive composition (I), a mixture of the reactive PDOS, the crosslinking agent, and a filler, and a viscosity reducing agent (III) are homogeneously mixed together; (1b) the homogeneous mixture is devolatilized, if necessary; (1c) a catalyst is homogeneously mixed with the devolatilized mixture;(2) the composition is shaped as desired; and (3) the composition is cured.

The pressure-adherent silicone elastomer compositions of the invention may be stored in various ways. They may be stored as two- (or more) part systems, so long as the ingredients in each part, as stored, are nonreactive, otherwise premature curing could occur. In one method of storing, the composition is stored in two packages wherein the first package contains all or part of the silicone pressure sensitive adhesive composition (I), all of the catalyst, and all or part of the reactive polydiorganosiloxane, and the second package contains the remaining portion of the silicone pressure sensitive adhesive composition (I), all of the crosslinking agent, and the remaining portion of the reactive polydiorganosiloxane.

For example, especially for those compositions which employ crosslinkable silicone elastomer compositions (II) based on ≡SiH/≡SiVi cure chemistry, a first part contains the silicone pressure sensitive adhesive composition (I), some of the reactive PDOS, all of the filler, all of the catalyst of the crosslinkable silicone elastomer composition (II), and the viscosity reducing agent (III), and a second part contains some of the reactive PDOS and all of the crosslinking agent of the crosslinkable silicone elastomer composition (II).

In another preferred method of storing, e.g., for those compositions which employ crosslinkable silicone elastomer compositions (II) based on ≡SiOH/alkoxy cure chemistry, a first part contains the silicone pressure sensitive adhesive composition (I), the reactive PDOS, the filler, the crosslinking agent of the crosslinkable silicone elastomer composition (II), and the viscosity reducing agent (III), and a second part contains the catalyst for the crosslinkable silicone elastomer composition (II).

Often it is preferred, when possible, to formulate the compositions of this invention into two or more parts where each part has the same or similar viscosity as the other for ease of mixing. Also, for ease of mixing, it is often desirable to formulate the parts so that the parts are to be mixed in a 1:1 volume to volume ratio.

The pressure-adherent silicone elastomers of the invention will adhere to many substrates, such as paper, cloth, glass cloth, silicone rubber, polyethylene, polyethylene terephthalate, polytitrafluoroethylene, glass, wood, metals, and skin. Therefore, there are many uses for the pressure-adherent silicone elastomers of this invention, where a coating or a body of pressure-adherent silicone elastomer is desirable. For examples, uses such as tapes and medical adhesives, such as wound dressings and bandages, or those adhesives used for sealing devices to the skin or for attaching prosthetic devices to the body can be achieved with the pressure-adherent silicone elastomer compositions of this invention. For example, when the compositions of this invention are employed to make tapes, formulations having suitable, low viscosities are selected for coating paper, as by knife coating or calendering, and the curing takes place after the paper is coated. Due to the low viscosities of the compositions of this invention, the coating process can be done without heat or the addition of volatile solvents. Depending on the desired use, it may be desirable to apply adhesion promoters on the substrate surface upon which the the pressure-adherent silicone elastomer composition will be placed.

The compositions of this invention are suitable as materials in devices for the controlled release of bioactive agents, such as drugs, herbicides, insecticides, pesticides, fertilizers, and pheromones. Specific to drugs, the materials are useful as the membrane in reservoir/membrane-type transdermal drug delivery systems and as the matrix material in matrix-type transdermal drug delivery systems.

When using a pressure-adherent silicone elastomer composition of this invention to form a membrane for controlling the delivery of a bioactive agent to a substrate, the method may comprise the steps of (1) contacting the substrate with a membrane formed from the composition of this invention and (2) contacting the membrane with a reservoir of the bioactive agent. In this case, the bioactive agent, in a controlled manner, passes through the membrane to the substrate. When using the pressure-adherent silicone elastomer compositions of this invention to form a matrix for controlling the delivery of a bioactive agent to a substrate, the method may comprise the step of contacting the substrate with a matrix formed from the composition of this invention which contains a bioactive agent. When referring to controlling drugs to a human or other animal, the bioactive agent is a drug and the substrate is the patient's body, i.e. the skin. A transdermal drug delivery device employing the composition of this invention would include a container for containing the drug, the drug contained within the container, and a pressure-adherent silicone elastomer on the container for maintaining contact between the container and a patient's skin wherein the pressure-adherent silicone elastomer is the cured form of the composition of the invention.

The compositions of this invention have many advantages, many of which were discussed above. It has been discussed that the compositions are devoid of volatile solvents, yet have a low enough viscosity for room temperature molding techniques. The absence of volatile solvents makes the process of manufacturing with the compositions safer and easier, since evaporating solvents do not have to be collected and contained away from the environment. The absence of volatile solvents also allows for the manufacture of thick sections of pressure-adherent silicone elastomer with minimal bubbling due to entrapped evaporating solvents. The thickness of a section capable of bubbling caused by the inclusion of volatile solvents depends upon the rate of curing. If curing is done quickly, the evaporating solvents have more of a chance to become entrapped. Usually, a "thick" section, which has the possibility of bubble entrapment, is considered to be as thin as 0.1-0.2 mm thick. Additionally, the compositions of this invention do not use flammable materials, such as xylene, benzene, and toluene, as opposed to many PSA's which contain such flammable solvents. The compositions of this invention also have formulation flexibility, i.e., they may be formulated with or without fillers and with various crosslinkable silicone elastomer compositions and still achieve a low-viscosity, moldable composition.

In addition, the pressure-adherent silicone elastomer compositions of this invention which employ some of the aforementioned esters as the viscosity reducing agent, have the potential advantage, when used in transdermal drug delivery applications, to provide additional benefits in terms of providing an increase and improved control of skin permeation rates and skin softening.

Employing the pressure-adherent silicone elastomer composition of this invention as a matrix type transdermal drug delivery device has the benefits of making manufacturing easier, because it eliminates the need for an adhesive coating on the matrix, since the matrix itself can adhere to the skin.

The following are examples of the invention and are meant to be illustrative only and should not be construed as limiting the invention which is properly delineated in the appended claims. In the following examples, all parts and percentages are by weight unless otherwise specified.

Unless otherwise stated, quantitative adhesion measurements reported herein were obtained through use of a one inch wide tape consisting of SCOTCH-PAK® 1109 Release Liner (an aluminized polyester film coated with a release coating available from the 3M Company, St. Paul, Minnesota) and a 2 mil layer of the pressure-adherent silicone elastomer. The tape was adhered to a stainless steel panel with a 4 lb. roller. The measurements were obtained by stripping the tape from the panel at a rate of 12 inches/minute at an angle of 180° while attached to a tensile testing machine, and the results were expressed in grams per centimeter.

Adhesive peel was measured by placing one gram of the material to be tested on each of three strips of clean, smooth 20 lb bond paper, centered 1 inch from one end. The strips were then allowed to sit undisturbed at 23° C. and 50% relative humidity (RH) for 10–15 minutes. A second strip of the same type of paper was placed over each of the first strips, and, with finger pressure, the strips were pressed together over the complete area covered by the material being tested. The three laminates were then allowed to stand undisturbed for 16–24 hours at 23° C. and 50% RH. The end of the laminate opposite from the applied material was then separated, and each separated end of paper was placed in a jaw of a Keil Tester, Model No. 2, (available from Billings Machine, Auburn, MI). The papers were then peeled apart at 18°. The maximum load required to separate the two strips of paper was recorded, and the average maximum load of the three laminates was reported in grams.

Unless otherwise stated, release values reported herein were obtained through use of a one inch wide tape consisting of SCOTCH-PAK® 1109 Release Liner and a 2 mil layer of the pressure adherent silicone elastomer. The tape was adhered to SCOTCH-PAK® 1006 Release Liner (also an aluminized polyester film coated with a release coating available from the 3M Company, St. Paul, Minnesota) with a 4 lb. roller. The release values were obtained by stripping the tape from the SCOTCH-PAK® 1006 Release Liner at a rate of 40 inches/minutes at an angle of 180° while attached to a tensile testing machine, with the results being expressed in grams per centimeter. An average value over the entire length of the liner is recorded.

Unless otherwise stated, non-volatile content of a material, hereinafter referred to as "N.V.C", was determined by placing 1.5 g of the material in an aluminum foil dish, 60 mm in diameter and 15 mm deep, and heating the sample for 1 hour at 150° C. in an air-circulating oven. The heated sample was then cooled to room temperature and reweighed to determine the weight of the non-volatile material (w). The N.V.C., in percent, is equal to 100*w/1.50.

All viscosities in the following examples were measured at about 25° C. unless otherwise stated.

For the following examples, PDMS Fluid A is a dimethylvinyl endblocked polydimethylsiloxane having a viscosity between 1800 and 2400 cp as measured by using a Brookfield Viscometer Model RVF, using spindle #2 at 10 rpm's.

PDMS Fluid B is a homogeneous mixture of hydroxyl endblocked polydimethylsiloxane having a number average molecular weight of approximately 40,000 and minor amounts of cyclic polydimethylsiloxane having degrees of polymerization between 4 and 30, the mixture having a viscosity between 12,000 and 15,000 cp as measured using a Brookfield Viscometer Model HAF with spindle #3 at 10 RPM's.

Resin A-1 is a xylene solution of a resinous copolymeric siloxane prepared from 45 parts of sodium silicate (41.6° Be) and 20 parts of Me$_3$SiCl according to the method of U.S. Pat. No. 2,676,182 to Daudt, et al. containing Me$_3$SiO$_\frac{1}{2}$ units and SiO$_{4/2}$ units in a ratio of approximately 0.75:1.0, and having a N.V.C. typically about 69–71%, an acid number in the range of 0.3 to 1.4, and a viscosity in the range of 10–14 centipoise at 25° C. at 60% N.V.C. in xylene solution, and a silicon-bonded hydroxyl content of about 2.5 weight percent based on a 100% N.V.C.

Resin A-2 is devolatilized Resin A-1 (100% N.V.C.).

PSA Composition A was prepared by homogeneously mixing 24.1 parts by weight of Resin A2, 39.8 parts by weight xylene, and 36.1 parts by weight PDMS Fluid B. The mixture was then heated to 100° C. and anhydrous ammonia was passed through the mixture at a rate of 11 ml/min/lb of non-volatile component of the mixture for 2 hours. To endcap the mixture, hexamethyldisilazane was then admixed at a 3:1 mole ratio of endblocking triorganosilyl to total silicon-bonded hydroxyl radicals present in the resin copolymer and polydiorganosiloxane, and the mixture was allowed to react for 3 hours at 95°–100° C. The mixture was then heated to 140° C. and maintained at 140° C. under reflux conditions for 3 hours to remove condensation water. The mixture was then stripped to greater than 90% N.V.C. The plasticity of the stripped mixture measured about 130–140 mils as measured by the technique described above.

PSA Composition B is a 35 weight percent PSA Composition A in trichlorotrifluoroethane solution.

PSA Composition C was prepared by removing the trichlorotrifluoroethane from PSA Composition B.

PSA Composition D is a pressure sensitive adhesive composition prepared by homogeneously mixing 60 parts of Resin A-1, 40 parts of PDMS Fluid b, and a portion of 2.4 parts of ammonium carbonate, heating the mixture to 100° C. and maintaining the temperature at 100° C. for 1 hour. Then the remaining portion of the 2.4 parts ammonium carbonate were added to the mixture, and mixing continued for another hour at 100° C. The mixture was then stripped for 16 hours at 100° C. to remove the volatile components. PSA Composition B cooled to room temperature had a specific gravity of 1.085–1.115, a N.V.C. of at least 98.8% where N.V.C. is defined as above except that a 1 g. sample was used and the temperature of the oven was 177° C., a plasticity of 150–200 measured after a 24 hour rest and after force was applied on a 2 gram specimen for 3 minutes ±5 seconds using ASTM D926, and, when dispersed in trichlorotrifluoroethane to an N.V.C. of 18.5%, the adhesive peel measures at least 1600 g.

PSA Composition E was prepared by homogeneously mixing 26.74 parts hydroxy-endblocked polydimethylsiloxane gum having a plasticity between 47 and 60 mils, 30.14 parts Resin A-2, 39.58 parts xylene, 3.40 parts isopropanol, and 0.14 parts of a mixture consisting of 9% tetramethylguanidine, 9% 2-ethyl hexoic acid, and 82% xylene. The plasticity of the gum was measured at room temperature and after force was applied on a 4.2 gram specimen for 3 minutes ±5 seconds using ASTM D926.

PSA Composition F is a 50 weight percent PSA Composition A in trichlorotrifluoroethane solution.

PSA Composition G is a solution consisting of 18.5 weight % PSA Composition D and 81.5 weight %. trichlorotrifluoroethane.

Catalyst A is a complex of divinyltetramethyldisiloxane and $H_2PtCl_6$.

Elastomer Composition A was prepared by homogeneously mixing 80 parts by weight of a polydimethylsiloxane of about 12,000 cp with about 5 to 15 percent of the endblocking being trimethylsiloxy endblocking and the remaining being hydroxy-endblocking and 13.71 parts by weight of DEGUSSA AEROSIL R972, a finely divided treated silica, to form a base. The base was then de-aired. 0.57 parts by weight of an 8:1 weight ratio mixture of dimethyl cyclic tetremer and stannous oleate and 5.71 parts by weight of a 1:1 weight ratio mixture of methyltriacetoxysilane and ethyltriacetoxysilane were homogeneously mixed with the base to form Elastomer Composition A.

Elastomer Composition B, Part I, was prepared by homogeneously mixing 1.18 parts by weight water, 5.75 parts by weight of hexamethyldisilazane, and 34.65 parts by weight of PDMS Fluid A. 23.67 g. fume silica were gradually mixed with the mixture. Under full vacuum (20 in. Hg), the mixture was heated to about 180° C., for about 2 hours, where timing started when the temperature reached 150° C. The mixture was then cooled to 115° C. and the vacuum released and 34.65 more parts by weight of PDMS Fluid A were slowly mixed into the mixture. When the temperature of the mixture fell below 50° C., 0.09 parts by weight of Catalyst A was mixed into the mixture.

Elastomer Composition B, Part II, was prepared by homogeneously mixing, for one hour, 88 parts by weight of PDMS Fluid A, 12 parts by weight of a trimethylsiloxy endblocked polyorganosiloxane having an average of five methylhydrogensiloxane units and three dimethylsiloxane units, and 0.4 parts of methylvinyl cyclics.

Elastomer Composition C, Part I, was prepared by homogeneously mixing 99.1 parts by weight of Elastomer Composition B, Part I, with 0.1 part by weight of Catalyst A.

Elastomer Composition D was prepared by homogeneously mixing 71.4 parts by weight of PDMS Fluid B, 24.3 parts by weight of Celite Super Floss silica filler, 2.1 parts by weight of normal propyl orthosilicate, and 2.1 parts by weight of a hydroxyl endblocked polydimethylsiloxane having a viscosity of about 0.04 Pa sec at 25° C.

Elastomer Composition E was prepared the same as Elastomer Composition B, Part I, with the exception that Catalyst A was not added.

The compositions of the following examples not only exhibited pressure sensitive adhesive properties allowing them to adhere to skin, but were also elastomeric in nature. Generally, what is meant by "elastomeric" and desired for this invention is that the cured material is flexible and cohesively holds together, so that there is no appreciable transfer of the pressure-adherent silicone elastomer to the release paper or substrate desired. The cured materials in the following examples fit this description. They were not "cheesy" as when some parts cohesively hold together and some do not. More specifically and more preferred, the material can be stretched or deformed to some degree without breaking and will return to substantially the same shape and size as it was originally.

EXAMPLE 1

The following example illustrates making a pressure-adherent silicone elastomer composition of the invention using a tin-catalyzed, moisture-curable crosslinkable silicone elastomer composition based on $H_2O/≡SiOCOCH_3$ cure chemistry.

40 g. Elastomer Composition A were homogeneously mixed with 3 g. isopropylpalmitate and 162.8 g. PSA Composition B (containing 57 g. PSA Composition A). The trichlorotrifluoroethane was stripped from the mixture at a temperature of 50° C. The stripped mixture was allowed to cure at room temperature for several days. The resulting cured product was tacky to the touch and had an elastomeric nature.

EXAMPLE 2

This example illustrates the use of a tin-catalyzed crosslinkable silicone elastomer composition based on ≡SiOH/alkoxy cure chemistry without the addition of a viscosity reducing agent (III).

31.75 g. Elastomer Composition D, 67.55 g. of PSA Composition F, and 9 drops of stabilized stannous octoate were homogeneously admixed and press-cured at about 100° C. The cured material was tacky to the touch and had an elastomeric nature.

EXAMPLE 3

This example illustrates the use of a crosslinkable silicone elastomer composition (II) based on ≡SiVi to ≡SiH cure chemistry.

36.14 parts by weight of Elastomer Composition B, Part I, 38.89 parts by weight of PSA Composition F, and 3.62 parts by weight of Elastomer Composition B, Part II, were homogeneously admixed and press-cured at about 100° C. The cured silicone material was tacky to the touch and had an elastomeric nature.

EXAMPLE 4

This example illustrates the use of the silicone pressure sensitive adhesive composition (I) and the crosslinkable silicone elastomer composition (II) employed in a weight ratio of about 19:81.

14.74 g. PSA Composition F, 28.24 g. Elastomer Composition B, Part I, and 3.00 g. Elastomer Composition B, Part II, were homogeneously mixed and press-cured at about 100° C. After curing, the silicone material was tacky to the touch and had an elastomeric nature.

EXAMPLES 5-7

This example illustrates compositions without using any filler material and also illustrates using various levels of viscosity reducing agent (III).

The compositions shown in Table 1 were prepared by this procedure: (1) heat PSA Composition A to 150° C., (2) slowly admix PDMS Fluid A, (3) cool the admixture to 100° C. or lower, (4) slowly admix isopropylpalmitate to the admixture, (5) cool the admixture to room temperature, (6) admix Catalyst A, (7) measure the viscosity of the cooled admixture using a Brookfield Viscometer Model HAF, using spindle #6 at three different rpm's, (8) add 3.58 parts by weight of Elastomer Composition B, Part II, based on 100 parts by weight of the total PSA Composition A, PDMS Fluid A, isopropylpalmitate, and Catalyst A admixture, (9) squeeze the composition to a 2 mil (0.051 mm) thickness between SCOTCH-PAK® 1109 and 1006 Release Liners, and (10) cure for 2 hours at 60° C. The viscosities of the admixtures are given in Table 2. The release, adhesion, and tack results are given in Table 3. The tack was found to increase with each example.

TABLE 1

| | Weight % in Composition | | |
|---|---|---|---|
| | Example 5 | Example 6 | Example 7 |
| PSA Composition A | 61.17 | 64.55 | 68.53 |
| PDMS Fluid A | 27.45 | 28.96 | 30.75 |
| isopropyl-palmitate | 11.35 | 6.45 | 0.69 |
| Catalyst A | 0.03 | 0.03 | 0.03 |

TABLE 2

| | Viscosity (cp.) | | |
|---|---|---|---|
| | at 10 RPM | at 5 RPM | at 2 RPM |
| Example 5 | 25,000 | — | — |
| Example 6 | 59,000 | 59,000 | — |
| Example 7 | — | 326,000 | 340,000 |

TABLE 3

| | Example 5 | Example 6 | Example 7 |
|---|---|---|---|
| Release (g/cm) | 30.12 | 44.88 | 108.40 |
| Adhesion from SS panel (g/cm) | 28.7 | 45.5 | 84.1 |
| Tack | good | good | good |

EXAMPLES 8-14

Examples 8-14 illustrate pressure-adherent silicone elastomers incorporating various drugs.

In Examples 8-13, compositions were prepared which consisted of 29.3 weight % Elastomer Composition B, Part I, 48.6 weight % PSA Composition C, 9.0 weight % isopropylpalmitate, 10.0 weight % of the selected bioactive agent, and 3.1 weight % of Elastomer Composition B, Part II. In Example 8, the bioactive agent was theophylline; Example 9, progesterone; Example 10, indomethacin; Example 11, 10% nitroglycerine on lactose; Example 12, testosterone; and Example 13, estradiol. In Example 14, the composition consisted of 32.55 weight % Elastomer Composition C, Part I, 55.45 weight % PSA Composition C, 10 weight % methyl salicylate, and 2 weight % Elastomer Composition B, Part II. In all of Examples 8-14, the cured materials were elastomeric in nature, exhibited good tack, and would be suitable for use as transdermal adhesives.

EXAMPLES 15-22

Examples 15-21 illustrate compositions using various levels of the silicone pressure sensitive adhesive composition (I).

In each example, 32.55 g. Elastomer Composition B, Part I, 10 g. isopropylpalmitate, and a selected amount of PSA Composition B were homogeneously mixed. In Example 15, 100 g. PSA Composition B were used; in Example 16, 128.57 g.; in Example 17, 185.71 g.; in Example 18, 228.57 g.; in Example 19, 285.71.; in Example 20, 342.85 g.; and in Example 21, 400 g. were used. The trichlorotrifluoroethane was then stripped from the mixture under vacuum either at room temperature or at 50° C. The compositions after stripping are given in Table 4. The viscosities of the stripped mixtures (prior to addition of the curing agent) were then measured using a Brookfield Viscometer Model HAF using spindle #7 at three different rpm's, and the values are reported in Table 5.

For a comparison, in Example 22 a pressure-adherent silicone elastomer composition not of the invention was prepared using a pressure sensitive adhesive, PSA Composition E, comprising a silicone resin and a silicone gum. PSA Composition E employs a silicone gum as the silicone fluid rather than a low-viscosity fluid, and the silicone resin and silicone fluid were not condensed, as they are in the compositions of the invention. The pressure-adherent silicone elastomer composition was prepared by homogeneously mixing 32.52 parts Elastomer Composition E and 97.71 parts PSA Composition E, removing the xylene by heating to 100° C. and pulling vacuum on the mixture, slowly adding 10 parts isopropylpalmitate to the xylene-free mixture, then allowing the mixing to cool and then adding 0.03 parts Catalyst A. The composition at this stage is also given in Table 4. The viscosity of the composition at this stage (prior to addition of the curing agent) as measured using a Brookfield Viscometer Model HAF using spindle #7 is given in Table 5. The composition of comparative Example 22 is between the compositions of Examples 16 and 17. As is evident in the comparison of the viscosities, the pressure-adherent silicone elastomer composition of the invention yields compositions having significantly lower viscosities than pressure-adherent silicone elastomer composition prepared using pressure sensitive adhesives which utilize silicone gums and are not condensed with the silicone resin.

TABLE 4

| | Grams of Component | | |
|---|---|---|---|
| Ex. # | Elastomer Comp. B, Part I | IPP | PSA Comp. C |
| 15 | 32.55 | 10 | 35 |
| 16 | 32.55 | 10 | 50 |
| 17 | 32.55 | 10 | 65 |
| 18 | 32.55 | 10 | 80 |
| 19 | 32.55 | 10 | 100 |
| 20 | 32.55 | 10 | 120 |
| 21 | 32.55 | 10 | 140 |
| 22 | 33.68 | 10.36 | 55.93 |

TABLE 5

| | Viscosity (poise) | | |
|---|---|---|---|
| | at 10 RPM | at 5 RPM | at 1 RPM |
| Example 15 | 1280 | 1840 | 3200 |
| Example 16 | 1640 | 2160 | 3600 |
| Example 17 | 2320 | 2560 | 2800 |
| Example 18 | 3120 | 3360 | 3600 |
| Example 19 | 1880 | 1920 | 2000 |
| Example 20 | 2520 | 2560 | 2800 |
| Example 21 | 3160 | 3280 | 3600 |
| Example 22 | — | — | 78400 |

3.45 g. Elastomer Composition B, Part II, were then added to the stripped mixtures of Examples 15-21, the mixture was cast 2 mils thick between SCOTCH-PAK® 1006 and 1109 Release Liners, and cured for 2 hours at 60° C. Table 6 gives the release, adhesion, and tack results. The tack was found to increase with each example.

TABLE 6

| | Release (g/cm) | Adhesion from SS panel (g/cm) | Tack |
|---|---|---|---|
| Ex. 15 | 10.66 | 13.0 | Fair |
| Ex. 16 | 16.99 | 18.7 | Good |
| Ex. 17 | 50.15 | 35.6 | Good |
| Ex. 18 | 67.73 | 58.0 | Good |
| Ex. 19 | 81.44 | 71.7 | Good |
| Ex. 20 | 125.37 | 157.9 | Good |
| Ex. 21 | 221.2 | 232.8 | Good |

EXAMPLES 23-27

Examples 23-27 show the use of silicone fluids of various viscosities used as the viscosity reducing agent (III).

In Examples 23-27, 65.10 g. Elastomer Composition B, Part I, 20 g. of a selected trimethyl-endblocked polydimethylsiloxane fluid, and 308.60 g. PSA Composition B were homogeneously mixed. In Example 23, the trimethyl-endblocked polydimethylsiloxane fluid had a viscosity of 5 cSt. at 25° C.; in Example 24, the fluid had a viscosity of 20 cSt.; in Example 25, 100 cSt.; in Example 26, 350 cSt.; and in Example 27, 12,500 cSt. The trichlorotrifluoroethane was then stripped from the mixture in each example under vacuum either at room temperature or at 50° C. and the viscosity of the mixture was then measured using a Brookfield Viscometer Model HAF. Then 6.90 g. Elastomer Composition B, Part II, were added to the stripped mixtures, each mixture was cast 2 mils thick between SCOTCH-PAK® 1006 and 1109 Release Liners, and cured for 2 hours at 60° C. Table 7 gives the viscosities of the mixtures as measured. Table 8 gives the release and adhesion results. All of the samples were tacky to the touch, with samples of Examples 26 and 27 had higher tack than did the others.

TABLE 7

| | Viscosity (poise) | | | |
|---|---|---|---|---|
| Spindle #/rpm: | 6/5 | 6/1 | 7/5 | 7/1 |
| Ex. 23 | 1800 | 1900 | — | — |
| Ex. 24 | 2860 | 2920 | — | — |
| Ex. 25 | 3120 | 2800 | — | — |
| Ex. 26 | — | 4400 | — | — |
| Ex. 27 | — | — | 10,400 | 9,600 |

TABLE 8

| | Release (g/cm) | Adhesion from SS panel (g/cm) | Tack |
|---|---|---|---|
| Ex. 23 | 42.77 | 32.5 | Fair |
| Ex. 24 | 58.00 | 34.2 | Fair |
| Ex. 25 | 58.94 | 30.4 | Fair |
| Ex. 26 | 77.21 | 36.8 | Fair |
| Ex. 27 | 109.9 | 66.8 | Good |

EXAMPLES 28-31

Examples 28-31 illustrate the use various levels of trimethyl-endblocked polydimethylsiloxane as the viscosity reducing agent (III).

In examples 28-31, 65.10 g. Elastomer Composition B, Part I, a selected amount of a trimethyl-endblocked polydimethylsiloxane (PDMS) having a viscosity of 12,500 cSt. at 25° C., and 308.60 g. PSA Composition B were homogeneously mixed together. For Example 28, 20 g. of the PDMS were used; for Example 29, 40 g. were used; for Example, 30, 50 g.; and for Example 31, 60 g. The trichlorotrifluoroethane was then stripped from the mixture by placing the mixture under vacuum either at room temperature or at about 50° C. and the viscosity of the mixture was measured using a Brookfield Viscometer HAF using spindle #7. Then for each example, 6.90 g. Elastomer Composition B, Part II, were added to the stripped mixture, the mixture was cast 2 mils thick between SCOTCH-PAK® 1006 and 1109 Release Liners, and cured for 2 hours at 60° C. Table 9 give the viscosities of the mixtures as measured. Table 10 gives the release, adhesion, and tack results.

TABLE 9

| | Viscosity (poise) | | |
|---|---|---|---|
| | at 10 RPM | at 5 RPM | at 1 RPM |
| Ex. 28 | — | 10,400 | 9,600 |
| Ex. 29 | 4,200 | 4,400 | 4,800 |
| Ex. 30 | 2,840 | 2,880 | 2,800 |
| Ex. 31 | 2,120 | 2,160 | 2,000 |

TABLE 10

| | Release (g/cm) | Adhesion from SS Panel (g/cm) | Tack |
|---|---|---|---|
| Ex. 28 | 109.9 | 66.8 | Fair |
| Ex. 29 | 75.46 | 40.1 | Fair |
| Ex. 30 | 66.91 | 34.5 | Good |
| Ex. 31 | 66.91 | 40.8 | Good |

EXAMPLES 32-33

Examples 32-33 illustrate the use of a tin-catalyzed, room temperature curing silicone elastomer composition which cures via ≡SiOH/alkoxy cure chemistry and illustrates varying the degree of crosslinking of the elastomer composition by adding different levels of crosslinking agent.

In Examples 32-33, 20 g. PDMS Fluid B, 211.4 g. PSA Composition B, 5 g. isopropylpalmitate, and a selected amount of ethylorthosilicate (the crosslinking agent) were homogeneously mixed together. For Example 32, 1.5 g. ethylorthosilicate were used and for Example 33, 2.0 g. ethylorthosilicate were used. The trichlorotrifluoroethane was then stripped from the mixture by placing the mixture under vacuum either at room temperature or at about 50° C. and the viscosity of the stripped mixture was measured using a Brookfield Viscometer Model HAF using spindle #6 at three different rpm's. Then for each example, dibutyltindilaurate was added to the stripped mixture at a level of 0.5 weight % based on the total weight of the PDMS Fluid B, PSA Composition B, isopropylpalmitate, and ethylorthosilicate mixture, the mixture was cast 2 mils thick between SCOTCH-PAK ® 1006 and 1109 Release Liners, and cured. Table 11 give the viscosities measured. Table 12 gives the release and adhesion results. In both examples, the tack was excellent.

TABLE 11

| | Viscosity (poise) | | |
|---|---|---|---|
| | at 10 RPM | at 5 RPM | at 1 RPM |
| Ex. 32 | 720 | 740 | 750 |
| Ex. 33 | 990 | 1000 | 1100 |

TABLE 12

| | Release (g/cm) | Adhesion from SS panel (g/cm) |
|---|---|---|
| Ex. 32 | 90.27 | 73.4 |
| Ex. 33 | 80.73 | 83.3 |

EXAMPLES 34-36

Examples 34-36 illustrate the use of various viscosity reducing agents and compare release and adhesion results with an example of not using a viscosity reducing agent.

The compositions given in Table 13 were prepared. For Example 35, the viscosity reducing agent was polyethylene glycol 400 monolaurate, and for Example 36, glycerol trioleate. The compositions were sheeted out on to SCOTCH-PAK ® 1022 Release Liner, a polyester film coated with a release coating available from the 3M Company, St. Paul, Minnesota, and cured open faced for 2 hours at approximately 60° C., with the exception that Example 36 was cured for 48 hours. SCOTCH-PAK ® 1006 Release Liner was then laminated to the cured samples. Release values measured from SCOTCH-PAK ® 1022 Release Liner, adhesion values measured from stainless steel.

TABLE 13

| | Weight % in Composition | | |
|---|---|---|---|
| | Ex. 34 | Ex. 35 | Ex. 36 |
| PDMS Fluid A | 29.76 | 27.97 | 27.97 |
| Catalyst A | 0.24 | 0.23 | 0.23 |
| PSA Composition B | 66.32 | 62.34 | 62.34 |
| Viscosity Reducing Agent | — | 6.00 | 6.00 |
| Elastomer Composition B | 3.68 | 3.45 | 3.45 |

TABLE 13-continued

| | Weight % in Composition | | |
|---|---|---|---|
| | Ex. 34 | Ex. 35 | Ex. 36 |
| Part II | | | |

TABLE 14

| | Release (g/cm) | Adhesion (g/cm) |
|---|---|---|
| Ex. 34 | 115.57 | 96.7 |
| Ex. 35 | 154.33 | 18.0 |
| Ex. 36 | 142.73 | 39.7 |

EXAMPLES 37-38

Examples 37 and 38 illustrate the use of room-temperature titanate curable crosslinkable silicone elastomer compositions.

For each Example 37 and 38, 31.5 g. of a block copolymer having the average structure:

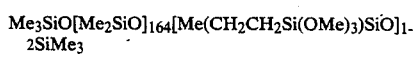

Me$_3$SiO[Me$_2$SiO]$_{164}$[Me(CH$_2$CH$_2$Si(OMe)$_3$)SiO]$_{1-2}$SiMe$_3$ and having a viscosity of about 1000 cp at 25° C. were blended with 185.71 g. PSA Composition B. The trichlorotrifluoroethane was removed by heating the blend to 50° C. under vacuum. Using a Brookfield Viscometer, Model HAF, spindle #6, the viscosity of the devolatilized blend was measured to be 195,000 cp. at 10 rpm's, 204,000 cp. at 5 rpm's, and 210,000 cp. at 2 rpm's. For Example 37, 3.5 g. tertiarybutyltitanate (TBT) were added to the devolatilized blend, and for example 38, 1.75 g. TBT were added. The compositions cured very quickly and were tacky to the touch.

EXAMPLES 39-40

In Examples 39-40, the compositions given in Table 15 were prepared.

TABLE 15

| | Ex. 39 | Ex. 40 |
|---|---|---|
| PDMS Fluid A (g.) | 32.55 | 32.55 |
| Isopropyl palmitate (g.) | 10.00 | 10.00 |
| PSA Composition G (g.) | 194.44 | 351.35 |
| Catalyst A (g.) | 0.23 | 0.23 |

The viscosities of these compositions are given in Table 16.

TABLE 16

| Spindle #/RPM: | 7/1 | 7/5 |
|---|---|---|
| Example 39 | 800 | 640 |
| Example 40 | 3400 | 2880 |

The compositions were then cast to 2 mil thickness between SCOTCH-PAK ® 1006 and a BIO-RELEASE ® liner (a coated release liner available from Akrosil, Menasha, WI, or H. P. Smith, a division of James River Corporation, Bedford Park, IL).

The release value measured from the BIO-RELEASE ® liner and the adhesion value measured from stainless steel are given in Table 17.

TABLE 17

| Example # | Release (g/cm) | Adhesion (g/cm) |
|---|---|---|
| 39 | 5.51 +/− 0.2 | 18.5 +/− 3.0 |
| 40 | 18.63 +/− 1.61 | 55.5 +/− 4.5 |

These and other variations of the present invention may be made which fall within the scope of the appended claims even though such variations were not specifically discussed above.

That which is claimed is:

1. A pressure-adherent silicone elastomer composition comprising a homogeneous mixture of:
   (I) a silicone pressure sensitive adhesive composition employed in an amount from about 15 to about 90 parts by weight, said silicone pressure sensitive adhesive composition comprising a homogeneous mixture of
      (A) from about 35 to about 70 parts by weight of at least one benzene-soluble resinous copolymer containing silicon-bonded hydroxyl radicals and consisting essentially of triorganosiloxy units of the formula $R_3SiO_{\frac{1}{2}}$ and tetrafunctionalsiloxy units of the formula $SiO_{4/2}$ in a ratio of about 0.6 to 0.9 triorganosiloxy units for each tetrafunctionalsiloxy unit present in the copolymer and
      (B) from about 30 to about 65 parts by weight of at least one polydiorganosiloxane consisting essentially of ARSiO units terminated with endblocking $TRASiO_{\frac{1}{2}}$ units, each said polydiorganosiloxane having a viscosity of from about 100 centipoise to about 50,000 centipoise at 25° C. where each T is —OH or —OR',
   where each R is a monovalent hydrocarbon radical having from 1 to 6 inclusive carbon atoms, each R' is an alkyl radical of from 1 to 4 inclusive carbon atoms, and each A radical is selected from the group consisting of R and halohydrocarbon radicals of from 1 to 6 inclusive carbon atoms,
   said silicone pressure sensitive adhesive composition having been reaction-condensed to a plasticity of not more than about 200 mils at 23° C. as measured after force is applied on a specimen weighing twice the specific gravity of the silicone pressure sensitive adhesive composition for 3 minutes ±5 seconds,
   (II) a non-reacted crosslinkable silicone elastomer composition which is curable by a chemistry which does not cure said silicone pressure sensitive adhesive composition (I) to the point of eliminating tack or adhesive properties employed in an amount from about 10 to about 85 parts by weight, the total of silicone pressure sensitive adhesive composition (I) and crosslinkable silicone elastomer composition (II) being 100 parts by weight, and
   (III) a non-volatile, nonflammable, compatible viscosity reducing agent for reducing the viscosity of said pressure-adherent silicone elastomer composition employed in an amount from 0 to about 40 weight percent based on the total weight of the silicone pressure sensitive adhesive composition (I) and the crosslinkable silicone elastomer composition (II), said viscosity reducing agent being generally nonreactive with said silicone pressure sensitive adhesive composition (I) and said crosslinkable silicone elastomer composition (II).

2. A composition as claimed in claim 1 wherein said silicone pressure sensitive adhesive composition has a plasticity of not more than 180 mils.

3. A composition as claimed in claim 1 wherein said silicone pressure sensitive adhesive composition has a plasticity of not more than 150 mils.

4. A composition as claimed in claim 1 wherein said polydiorganosiloxane has a viscosity of from 100 centipoise to 20,000 centipoise at 25° C.

5. A composition as claimed in claim 1 wherein said polydiorganosiloxane has a viscosity of from 100 centipoise to 15,000 centipoise at 25° C.

6. A composition as claimed in claim 1 wherein said pressure-adherent silicone elastomer composition is substantially free of flammable materials.

7. A composition as claimed in claim 1 wherein said silicone pressure sensitive adhesive composition is reaction-condensed at a temperature of at least 90° C. for at least 1 hour in the presence of a silanol condensation catalyst.

8. A pressure-adherent silicone elastomer composition as claimed in claim 1 wherein said crosslinkable silicone elastomer composition (II) comprises a reactive polydiorganosiloxane, a crosslinking agent, and, if necessary, a catalyst, wherein said reactive polydiorganosiloxane reacts with said crosslinking agent to form a crosslinked silicone elastomer.

9. A composition as claimed in claim 1 wherein said viscosity reducing agent (III) is employed in an amount from 0 to about 10 weight percent based on the total weight of the silicone pressure sensitive adhesive composition (I) and the crosslinkable silicone elastomer composition (II), and said pressure-adherent silicone elastomer composition, prior to initiating cure, has a viscosity of less than about 20,000 poise at 25° C. without the inclusion of volatile solvents.

10. A composition as claimed in claim 9 wherein said pressure-adherent silicone elastomer composition has a viscosity of less than about 10,000 poise at 25° C.

11. A composition as claimed in claim 10 wherein said pressure-adherent silicone elastomer composition has a viscosity of less than about 3,000 poise at 25° C.

12. A pressure-adherent silicone elastomer composition as claimed in claim 1 wherein said viscosity reducing agent is selected from the group consisting of polydiorganosiloxanes, polysilicates, 2-octyldodecanol, oleyl alcohol, phenylethanol, myristic acid isopropyl ester, caprylic/capric acid laurylstearyl ester, lauric acid hexyl ester, propionic acid myristyl ester, isostearic acid ethyl-lauryl ester, oleic acid ethyl ester, acetic acid phenyl ester, benzoic acid benzyl ester, salicylic acid methyl ester, lauric acid mono-1,1-propanediol ester, fatty acid polyethyleneglycol ester, caprylic/capric acid-1,2-propanediol diester, caprylic/capric acid glycerol monoester, lauric acid glycerol diester, butyric acid glycerol triester, caprylic/capric/lauric acid glycerol triester, acetic/stearic/oleic acid glycerol triester, adipic acid butyl ester, sebacic acid dibutyl ester, phthalic acid ester, citric acid triethyl ester, didecyl ether, fatty alcohol polyethyleneglycol ether, alkyl-aryl polyethyleneglycol ether, anisol, and methylnonylketone.

13. A pressure-adherent silicone elastomer composition as claimed in claim 1 wherein said viscosity reducing agent is an ester which is fluid at 25° C. and has the formula:

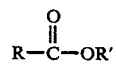

wherein R is a monovalent hydrocarbon radical having from 2 to 32 carbon atoms, and R' is a monovalent hydrocarbon radical having from 1 to 14 carbon atoms.

14. A pressure-adherent silicone elastomer composition as claimed in claim 13 wherein R has from 10 to 19 carbon atoms and R' has from 1 to 3 carbon atoms.

15. The cured composition formed from the composition of claim 1.

16. A method of forming a pressure-adherent silicone elastomer comprising the steps of:
   (a) preparing the pressure-adherent silicone elastomer composition as claimed in claim 1,
   (b) shaping the pressure-adherent silicone elastomer composition in the desired form for curing, and
   (c) curing the pressure-adherent silicone elastomer composition for a sufficient time to form the pressure-adherent silicone elastomer.

17. A kit for making a pressure-adherent silicone elastomer comprising:
   a first package and a second package,
   wherein said first package contains a composition comprising
   a first portion of (I) a silicone pressure sensitive adhesive composition comprising a homogeneous mixture of
   (A) from about 35 to about 70 parts by weight of at least one benzene-soluble resinous copolymer containing silicon-bonded hydroxyl radicals and consisting essentially of triorganosiloxy units of the formula $R_3SiO_{\frac{1}{2}}$ and tetrafunctionalsiloxy units of the formula $SiO_{4/2}$ in a ratio of about 0.6 to 0.9 triorganosiloxy units for each tetrafunctionalsiloxy unit present in the copolymer and
   (B) from about 30 to about 65 parts by weight of at least one polydiorganosiloxane consisting essentially of ARSiO units terminated with endblocking $TRASiO_{\frac{1}{2}}$ units, each said polydiorganosiloxane having a viscosity of from about 100 centipoise to about 50,000 centipoise at 25° C. where each T is —OH or —OR', where each R is a monovalent hydrocarbon radical having from 1 to 6 inclusive carbon atoms, each R' is an alkyl radical of from 1 to 4 inclusive carbon atoms, and each A radical is selected from the group consisting of R and halohydrocarbon radicals of from 1 to 6 inclusive carbon atoms,
   said silicone pressure sensitive adhesive composition having been reaction-condensed to a plasticity of not more than about 200 mils at 23° C. as measured after force was applied on a specimen weighing twice the specific gravity of the silicone pressure sensitive adhesive composition for 3 minutes ±5 seconds, and
   a catalyst and a first portion of a reactive polydiorganosiloxane, and
   said second package contains a composition comprising
   a second portion of said silicone pressure sensitive adhesive composition (I),
   a crosslinking agent, and a second portion of said reactive polydiorganosiloxane,
   wherein, after combining the contents of said first and second packages, said portions of said reactive polydiorganosiloxane, said catalyst, and said cross-linking agent together make a non-reacted crosslinkable silicone elastomer composition (II) which is curable by a chemistry which does not cure said silicone pressure sensitive adhesive composition (I) to the point of eliminating tack or adhesive properties, and, in said parts, said silicone pressure sensitive adhesive composition (I) is employed from about 15 to about 90 parts by weight and said crosslinkable silicone elastomer composition (II) is employed from about 10 to about 85 parts by weight, wherein the total of silicone pressure sensitive adhesive composition (I) and crosslinkable silicone elastomer composition (II) being 100 parts by weight and wherein said portions of said silicone pressure sensitive adhesive composition and of said reactive polydiorganosiloxane may be the same or different and may each be from 0 to 100 percent of the total required amount so long as the portions respectively total 100 percent of the required amount.

18. A pressure-adherent silicone elastomer composition as claimed in claim 1 wherein said silicone pressure sensitive adhesive composition (I) is employed in an amount from 40 to 80 parts by weight and said crosslinkable silicone elastomer composition (II) is employed in an amount from 20 to 60 parts by weight.

* * * * *